(12) United States Patent
Viscogliosi et al.

(10) Patent No.: US 11,497,707 B2
(45) Date of Patent: Nov. 15, 2022

(54) COMPOSITION FOR STRAIGHTENING HAIR

(71) Applicant: DI VISCO, Saint Genis Laval (FR)

(72) Inventors: Sébastien Frédéric Viscogliosi, Lyons (FR); Isabel Garcia, Lyons (FR); Didier Guerin, Saint Félix Laugarais (FR)

(73) Assignee: DI VISCO, Saint Genis Laval (FR)

( * ) Notice: Subject to any disclaimer, the term of this patent is extended or adjusted under 35 U.S.C. 154(b) by 74 days.

(21) Appl. No.: 16/630,745

(22) PCT Filed: Jul. 10, 2018

(86) PCT No.: PCT/FR2018/051730
§ 371 (c)(1),
(2) Date: Jan. 13, 2020

(87) PCT Pub. No.: WO2019/012219
PCT Pub. Date: Jan. 17, 2019

(65) Prior Publication Data
US 2020/0163867 A1     May 28, 2020

(30) Foreign Application Priority Data

Jul. 11, 2017   (FR) ..................... 17/56543
Nov. 24, 2017   (FR) ..................... 17/61139

(51) Int. Cl.
| A61K 8/92 | (2006.01) |
| A61K 8/34 | (2006.01) |
| A61K 8/44 | (2006.01) |
| A61K 8/64 | (2006.01) |
| A61Q 5/06 | (2006.01) |

(52) U.S. Cl.
CPC ............... *A61K 8/922* (2013.01); *A61K 8/34* (2013.01); *A61K 8/44* (2013.01); *A61K 8/64* (2013.01); *A61Q 5/06* (2013.01)

(58) Field of Classification Search
None
See application file for complete search history.

(56) References Cited

U.S. PATENT DOCUMENTS

| 6,871,652 | B1* | 3/2005 | Mueller ................... A61K 8/03 |
| | | | 132/202 |
| 9,381,144 | B1* | 7/2016 | Hilt ....................... A61Q 19/00 |
| 2009/0111750 | A1 | 4/2009 | Kelly et al. |
| 2013/0340785 | A1* | 12/2013 | Baum ................... A61K 8/4913 |
| | | | 132/206 |
| 2014/0302101 | A1* | 10/2014 | Carson .................... A61K 8/73 |
| | | | 424/401 |

FOREIGN PATENT DOCUMENTS

| FR | 3 030 241 A1 | 6/2016 |
| JP | 2001-010936 A | 1/2001 |
| JP | 2003-055166 A | 2/2003 |
| JP | 2008-231098 A | 10/2008 |
| JP | 2012-171897 A | 9/2012 |
| WO | 2011/104282 A2 | 9/2011 |

OTHER PUBLICATIONS

Sep. 28, 2018 International Search Report issued in International Patent Application No. PCT/FR2018/051730.
Sep. 28, 2018 Written Opinion of the International Searching Authority issued in International Patent Application No. PCT/FR2018/051730.
Product Information for "Botanist botanical scalp treatment" available from www.cosmetic-Info.jp <http://www.cosmetic-Info.jp>, Release date Aug. 1, 2016.

* cited by examiner

*Primary Examiner* — H. Sarah Park
(74) *Attorney, Agent, or Firm* — Oliff PLC

(57) ABSTRACT

A new composition allowing straightening hair including an amino acid, a protein, an alcohol and a vegetable oil, as well as a method for straightening hair implementing the composition.

3 Claims, 9 Drawing Sheets

*Figure 1 – Picture of the hair before treatment with the composition according to the invention*

*Figure 2 – Analysis under the microscope of the structure of a hair before treatment with the composition according to the invention*

*Figure 3 – Picture of the hair after treatment with the composition according to the invention*

*Figure 4 – Analysis under the microscope of the structure of a hair after treatment with the composition according to the invention*

*Figure 5 – Picture of the hair before treatment with the composition according to the invention*

*Figure 6 – Picture of the hair after treatment with the composition according to the invention*

Figure 7 – Picture of the hair after treatment with the composition according to the invention and after steam treatment

*Figure 8 – Picture of the hair before straightening treatment with the straightening composition containing only an amino acid and an alcohol*

Figure 9 – Picture of the hair after treatment with the composition containing only an amino acid and an alcohol

COMPOSITION FOR STRAIGHTENING HAIR

The present invention relates to a new composition allowing the straightening of hair comprising an amino acid, a protein, an alcohol and a vegetable oil, as well as a method for straightening the hair implementing said composition.

In the hair field, hair straightening is a hair styling technique that allows straightening hair temporarily or for a longer period of time.

Consumers wishing to straighten their hair not only seek to obtain a straightened hair having a good hold but also to obtain a result that lasts over time, in particular by withstanding subsequent shampoos.

To modify the shape of the hair, in a long lasting manner, heat treatments are generally used. These treatments enable a visual modification of the appearance of the hairstyle, both in terms of curl or frizz and in terms of overall volume of the hair. Such treatments result in a smoother visual appearance, a substantial gain in brilliance, resistance to moisture and heat for maintaining the hairstyle the day long.

These heat treatments are generally supplemented (or preceded) by «chemical» treatments of the hair with particular compositions.

A first complementary treatment involves the use of thiol reducers-based compositions. These technologies require a rigorous respect of the conditions of application recommended by the suppliers, in particular in terms of quantity and rest time. Furthermore, they may be contraindicated on overly sensitized hair and not be compatible with the application on the same day of other treatments such as coloration or discoloration. Moreover, they are smelly.

A second complementary treatment involves the use of compositions based on formalin (or formaldehyde) and its derivatives. These treatments have the particularity to be robust, perfectly compatible with all other conventional hair treatments, such as thiol straightening mentioned above, alkaline straightening, coloring or discoloration of all types, performed before or after. They give the hair an excellent hold, a very strong brilliance and an ease of daily care. However, these products require the use of a hair straightener at a temperature of 180-230° C. which very strongly damages the hair in the short or medium term. Furthermore, these straightening methods are also very long to apply because it is necessary to work strand by strand and the average overall time to straighten hair of the «Afro-Caribbean» type is 4 to 9 hours. Finally, for toxicological reasons, the use of some of these compounds is now prohibited and/or regulated.

Thus, new complementary treatments have been developed to facilitate the straightening process and to avoid the use of these substances which are toxic and harmful to the health of users.

Thus, the international patent application WO 2011/104282 describes the use of acid-based compositions, in particular the glyoxylic acid. This application describes in particular a method for semi-permanently straightening the hair, which consists in applying an alpha-ketoacid solution to the hair for 15 to 120 minutes, then drying and finally straightening with a hair straightener, at a temperature of approximately 200° C., the hair. The alpha-ketoacid that is used is preferably the glyoxylic acid.

In turn, the French patent application FR 3030241 describes a method for straightening the hair by applying a composition comprising an amino acid and a polyol followed by a straightening step by means of a hair straightener at a temperature of at least 100° C.

Nonetheless, it has been found that the glyoxylic acid may be not well tolerated, particularly when the scalp is sensitive and/or irritated. Its volatility, amplified by the use heat of the hair straightener, is also problematic.

Furthermore, all newly developed complementary treatments are ultimately ineffective or, at the very least, of limited effectiveness, and all require the use of a hair straightener at high temperature, which deteriorate the hair causing in particular their breakage.

Thus, at the date of the present invention, it is still necessary to develop a composition allowing the straightening of hair in a sustainable and efficient way under conditions of easy application without deteriorating the quality of the hair.

Yet, there has now been found a composition allowing for an effective and long lasting hair straightening, according to a method of application which is easy to implement while preserving the quality of the hair.

The object of the present invention is therefore a composition for straightening hair comprising:

an amino acid;
a protein;
an alcohol; and
a vegetable oil.

The composition according to the present invention allows for an effective and long lasting hair straightening, according to an easier method of application and preserving the quality of the hair, in particular by not using the hair straightener.

DETAILED DESCRIPTION

Figure 1:
FIG. 1 shows hair before treatment with the composition according to the invention.

In the context of the present invention:

the term «straightening» means any treatment allowing flattening or straightening the hair in order to give it a straightened apparent surface;

the term «amino acid» means any amino acid known to those skilled in the art, in particular the amino acids of general formula (I) or (II) below

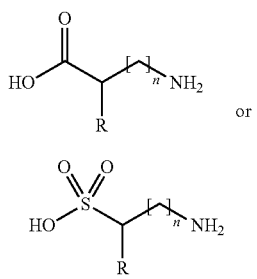

in which
R represents a hydrogen atom, a $C_1$-$C_5$-alkyl group possibly substituted with at least one group selected from hydroxyl, amino; —C(O)—OH; —S(O)$_2$—OH; —C(O)—O$^-$, M+; —S(O)$_2$—O$^-$, M+;

M+ representing a cationic counter ion such as an alkali metal, an alkaline-earth metal, or ammonium;

n is 0 or 1;

as well as their betaine forms; their optical isomers; solvates such as hydrates, and their acid or base, organic or mineral salts;

said amino acids being possibly grafted onto a heteromolecule which may be a silicone, a glucidic compound, a fatty acid or derivative thereof, a surfactant of anionic, cationic, non-ionic or amphoteric nature;

the term «vegetable oil» means any fatty substance extracted from an oleaginous plant, that is to say a plant whose seeds, nuts or fruits contain lipids;

the term «protein» means any protein, heteroprotein or protein derivative such as a protein grafted on a heteromolecule which may be a silicone, a glucidic compound, a fatty acid or derivative thereof, a surfactant of anionic, cationic, non-ionic or amphoteric nature, of variable size and shape, formed by one or several chain(s) charged with amino acids and bonded by peptide bonds. Preferably, the protein has a tertiary or quaternary structure;

the term «$C_x$-$C_y$-alkyl» means a straight or branched saturated hydrocarbon chain, and including from x to y carbon atoms;

the term «alcohol» means any straight or branched carbon chain containing from 1 to 10 carbon atoms substituted with a hydroxyl group, an amino alcohol, an aldol or a ketol. Preferably, «alcohol» refers to any straight or branched compound of the formula $C_nH_{2n+1}$ OH in which n is an integer comprised between 1 and 10; and the term «polyol» means any $C_1$-$C_{10}$-alkyl group substituted with at least two hydroxyl groups. Preferably, the term «polyol» means any compound selected from glycerin, propylene glycol, propane-1,3-diol or sorbitol.

In addition, in the context of the present invention, and unless stated otherwise, the proportions expressed in % correspond to weight percentages with respect to the total weight of the considered entity.

The composition according to the present invention therefore contains an amino acid, a protein, an alcohol and a vegetable oil. Preferably, the present invention relates to a composition as previously described having the following features, considered alone or in combination:

the amino acid is a proteinogenic amino acid or one of its acid or base, organic or mineral salts. More preferably, the amino acid is selected from aspartic acid, glutamic acid, asparagine, carnitine, cysteine, glutamine, histidine, leucine, isoleucine, methionine, N-phenylalanine, proline, hydroxyproline, threonine, tryptophan, tyrosine, valine, glycine, alanine, serine, beta alanine, taurine, lysine and arginine or one of their acid or base, organic or mineral salts. Most preferably, the amino acid is selected from glutamic acid, cysteine and arginine;

the protein is selected from possibly hydrolyzed creatine, possibly hydrolyzed keratin, possibly hydrolyzed wheat protein, possibly hydrolyzed silk protein, possibly hydrolyzed soy protein, possibly hydrolyzed collagen, possibly hydrolyzed elastin, possibly hydrolyzed pea protein, possibly hydrolyzed rice protein, possibly hydrolyzed conchiolin protein and possibly hydrolyzed whey protein. Most preferably, the protein is selected from creatine, keratin, possibly hydrolyzed wheat protein, possibly hydrolyzed silk protein and possibly hydrolyzed soy protein.

the alcohol is selected from butanol, isopropanol and ethanol. More preferably, the alcohol is selected as ethanol;

the vegetable oil contains at least 1% of sulfur or sulfur amino acids. More preferably, the vegetable oil is selected from sweet almond oil, olive oil, argan oil, Haarlem oil, Babassu oil, broccoli seed oil, avocado oil, linseed oil, apricot oil, cucumber oil, nigella oil, brazil nut oil, grape seed oil, shea olein, sesame oil and tomato oil. Most preferably, the vegetable oil is selected as broccoli seed oil or Haarlem oil;

the composition further contains a polyol; and/or the composition also contains pigments or dyes allowing obtaining a coloration of the hair.

The composition according to the invention may be in the form of a single composition or in the form of a kit comprising two, three or four separate compositions each containing one or more of the ingredients of the composition according to the present invention. Preferably, the present invention also relates to a kit useful for straightening hair comprising:

on the one hand, a composition containing the amino acid as previously defined and the protein as previously defined; and on the other hand, a composition containing the alcohol as previously defined and the vegetable oil as previously defined.

Preferably, the present invention relates to a kit as previously described having the following features, considered alone or in combination:

the kit contains from 50% to 70% of the composition comprising the amino acid and the protein and from 30% to 50% of the composition comprising the alcohol and the vegetable oil;

the composition containing the amino acid and the protein contains from 0.1% to 20% of amino acid as previously defined, preferably from 0.1% to 5% of amino acid as previously defined, more preferably from 0.1% to 1% of amino acid as previously defined;

the composition containing the amino acid and the protein contains from 0.1% to 20% of protein as previously defined, more preferably from 0.1% to 5% of protein as previously defined, and most preferably from 0.1% to 2% of protein as previously defined;

the composition containing the amino acid and the protein is in the form of a cream, gel, oil-in-water or water-in-oil emulsion, hair lotion or shampoo. More preferably, the composition containing the amino acid and the protein is in the form of a cream;

the composition containing the alcohol and the vegetable oil is in the form of a cream, gel, oil-in-water or water-in-oil emulsion, bi-phasic lotion or shampoo. More preferably, the composition containing the alcohol and the vegetable oil is in the form of a bi-phasic lotion;

the composition containing the alcohol and the vegetable oil contains from 1% to 50% of alcohol as previously defined, more preferably from 10% to 50% of alcohol as previously defined, and most preferably from 10% to 30% of alcohol as previously defined;

the composition containing the alcohol and the vegetable oil contains from 50% to 95% of vegetable oil as previously defined, more preferably from 50% to 80% of vegetable oil as previously defined, and most preferably from 70% to 80% of vegetable oil as previously defined;

the composition containing the alcohol and the vegetable oil further contains a polyol; and/or the pigments or dyes for the hair coloring are integrated in the preparation containing the amino acids and the proteins or in a complementary preparation.

The composition according to the present invention, whether in the form of a kit or not, may be applied according to any method known to those skilled in the art. Preferably, the composition according to the present invention is applied according to the method comprising the following steps:

when the composition is in the form of a kit as previously described, mixing the composition comprising the amino acid and the protein as previously defined and the composition comprising the alcohol and the vegetable oil as previously defined in order to obtain the composition according to the present invention;

applying the obtained product (that is to say the composition according to the present invention) strand by strand from the root to the tip;

leaving the product to act for a period that may vary from 15 minutes to 45 minutes;

drying the hair, preferably with hot air for example using a hair dryer;

rinsing the hair with water; and proceeding with styling with a hair dryer.

The method according to the present invention can be easily implemented and allows for an effective and long lasting hair straightening without the use of a hair straightener, thus preserving the quality of the hair.

The method according to the present invention may further be completed by:

the application of a shampoo prior to the application of the composition according to the invention;

a partial pre-drying of the hair before the application of the composition according to the invention; and/or the application of a composition of the hair «mask» type, whether hydrophobic or not, after rinsing with water and before styling the hair.

The present invention is illustrated in a non-limiting manner by the following examples.

EXAMPLE 1—KIT ACCORDING TO THE INVENTION

A kit containing:

a straightening composition in the form of a cream comprising an amino acid and a protein;

and a bi-phasic activator in the form of a bi-phasic lotion comprising an alcohol and a vegetable oil;

whose compositions are reported respectively in the following Tables 1 and 2 is prepared.

TABLE 1

Straightening composition

| Ingredients | Quantity (% w/w) |
|---|---|
| Glutamic acid | 0.1 |
| Cysteine HCl | 0.3 |
| Arginine | 0.1 |
| Creatine | 0.05 |
| Hydrolyzed wheat protein | 0.3 |
| Hydrolyzed soy protein | 0.3 |
| Hydrolyzed Keratin | 0.3 |
| Polyquaternium 7 | 0.25 |
| Hydroxypropyl starch phosphate | 0.25 |
| Perfume | 0.3 |
| Phenoxyethanol | 0.3 |
| Amisol Trio ™ | 0.2 |
| Phospholipids | |
| *Glycine soya* oil | |
| Glycolipids | |
| *Glycine soya* sterol | |
| Ascorbic acid | 0.05 |
| Cetearyl alcohol | 4 |
| Cetrimonium chloride | 2 |
| Ceteareth 20 | 0.3 |
| Glycerin | 0.25 |
| Ethylhexyl palmitate | 0.25 |
| *Triticum vulgare* (wheat germ oil) | 0.25 |
| *Orbignya oleifera* (Babassu seed oil) | 0.25 |
| Lactic acid | 0.05 |
| Citric acid | 0.05 |
| Ceramide-3 | 0.05 |
| BHT | 0.05 |
| PEG 90 M | 0.1 |
| Water | 89.35 |

TABLE 2

Bi-phasic activator

| Ingredients | Quantity (% w/w) |
|---|---|
| Broccoli seed oil | 75 |
| Ethanol | 20 |
| Glycerin | 2.5 |
| Water | 2.5 |

EXAMPLE 2—STRAIGHTENING TEST 2.1—Straightening Method

Figure 2:
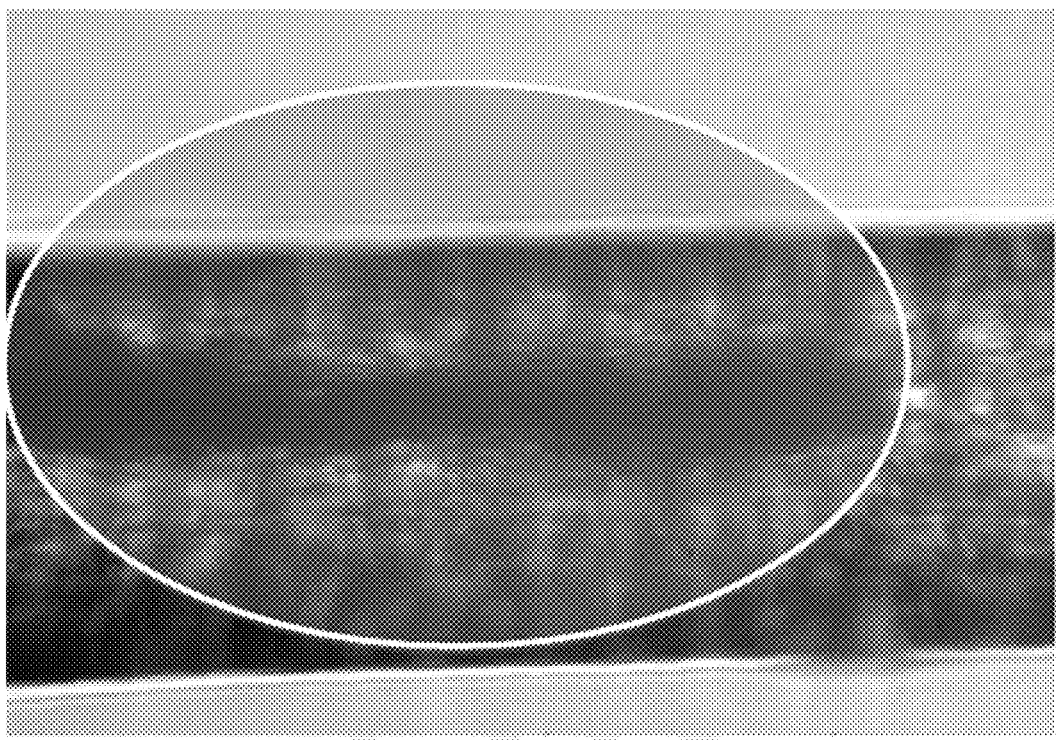
FIG. 2 shows microscopic analysis of the structure of the hair before treatment with the composition according to the invention.

The kit described in the previous Example 1 is used to straighten a hair of the afro type, very weakened by ancient straightening with thio acid until a significant break over the entire portion of the tray preventing any use of strong reductant-based products (FIG. 1). Microscopic analysis of a hair before treatment reveals an obvious corrosion of the inner structure (FIG. 2).

The application of the composition according to the invention is performed according to the following protocol.

Step 1: Hair Preparation

A double shampoo is performed using a preparer shampoo.

Step 2: Preparation of the Composition According to the Invention

The straightening composition and the bi-phasic activator of Example 1 are mixed in a straightening composition/bi-phasic activator dilution ratio of 60/40.

Step 3: Application of the Composition According to the Invention

The hair is detangled and pre-dried at 70% using a hair dryer.

The composition according to the invention is applied strand by strand from the root to the tip. Each strand is kneaded and combed in order to properly distribute the product.

Afterwards, the hair is covered with a cellophane and the composition is left to act for 30 minutes.

Step 4: Drying

Afterwards, the hair is dried in hot air with a hair dryer, by directing the blow of air from the root to the tip to lower the cuticle. 3 cm-wide strands are selected and maintained perpendicular to the scalp in order to be 100% dried.

Step 5: Rinsing

Afterwards, the hair is allowed to cool and the hair is rinsed with water. Then, a conventional «mask» composition is applied and allowed to act for 5 minutes before rinsing the hair again with water.

Step 6: Straightening

Afterwards, the hair is hand-styled with a hair dryer.

2.2—Obtained Results

It is observed that during straightening, the hair is directly straightened and put in place without the need to use a hair straightener.

Figure 3:
FIG. 3 shows the hair after treatment with the composition according to the invention.
Figure 4:
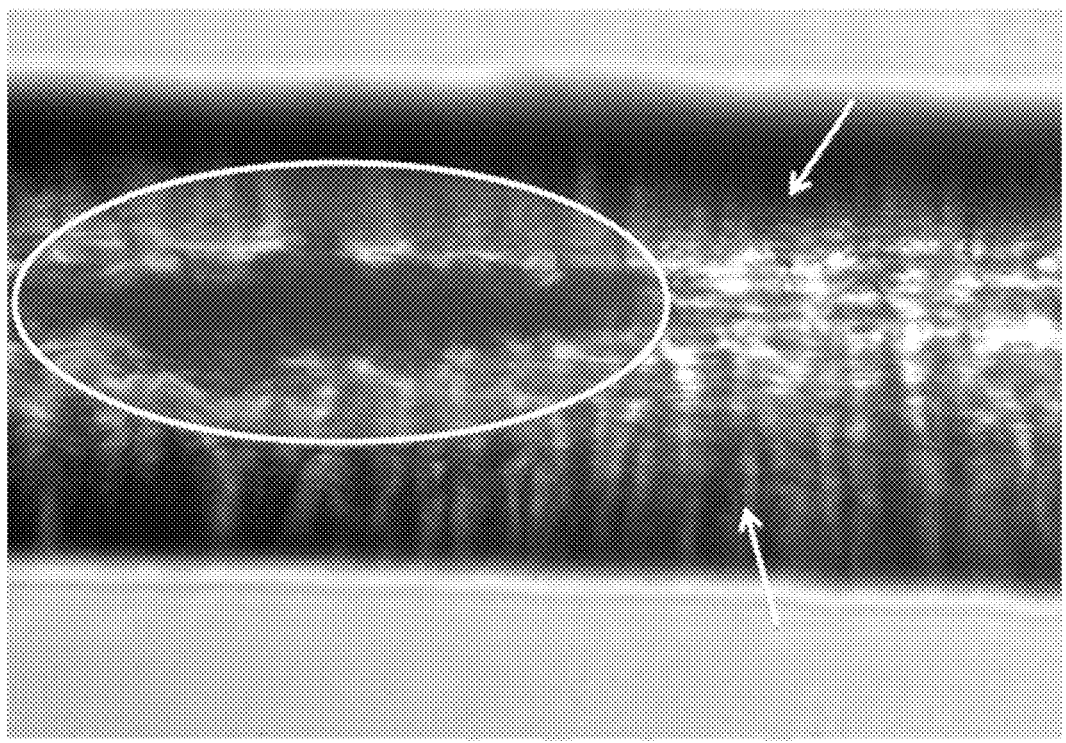
FIG. 4 shows microscopic analysis of the structure of the hair after treatment with the composition according to the invention.

A straightened hair is thus obtained simply in contact with the heat of the hair dryer, without resorting to the effect of tension or intense heat of the hair straightener. The volume is controlled and there is a significant reconstruction effect of this fiber which was previously sensitized (FIG. 3). The microscopic analysis of a hair after treatment also reveals the presence of straightening over the entire surface of the fiber as well as an improvement of the inner structure in comparison with the hair before treatment (FIG. 4).

An intense brilliance is observed and the hair has recovered a considerable fluidity and lightness.

Furthermore, the observed effects are long lasting (approximately three months).

EXAMPLE 3—KIT ACCORDING TO THE INVENTION

A kit containing:
- a straightening composition in the form of a straightening cream comprising an amino acid, a protein, an alcohol and a vegetable oil;
- and a «top coat» mask comprising a protein and a hydrophobic resin;

whose compositions are reported respectively in the following Tables 3 and 4 is prepared.

TABLE 3

Straightening composition

| Ingredients | Quantity (% w/w) |
| --- | --- |
| Hydrolyzed wheat protein | 4 |
| Hydrolyzed Keratin | 4 |
| Broccoli seed oil | 18 |
| Glycerin | 3.7 |
| Arginine | 0.8 |
| Cysteine | 1 |
| Glutamic acid | 0.4 |
| Maltose | 1 |
| Alcohol | 3.8 |
| Caprylic capric triglyceride | 5 |
| Tocopherol | 0.2 |
| Aloe vera juice | 20 |
| Coconut oil | 8 |
| Glyceryl stearate citrate | 2 |
| Hydroxypropyl starch phosphate | 3 |
| Cetearyl alcohol | 2 |
| Sodium stearoyl lactylate | 1 |
| Ceteareth-20 | 3 |
| Phenoxyethanol | 0.5 |
| Dehydroacetic acid, benzyl alcohol | 0.4 |
| Perfume | 0.5 |
| Water | 17.7 |

TABLE 4

«top coat» mask

| Ingredients | Quantity (% w/w) |
| --- | --- |
| Water | 77.6 |
| Cetearyl alcohol | 3.5 |
| Cetrimonium chloride | 6.6 |
| Glycerin | 0.5 |
| Babassu oil | 0.5 |
| Behentrimonium methosulfate, cetearyl alcohol | 2 |
| Wheat germ oil | 0.5 |
| Polyquaternium-7 | 0.5 |
| Shea Butter | 2 |
| Cetrimonium chloride, amodimethicone, trideceth-12 | 1 |
| Lactic acid | 0.05 |
| Phenoxyethanol | 0.4 |
| Hydrolyzed Keratin | 1 |
| Triacontanyl PVP (waterproof resin) | 1 |
| Hydrolyzed collagen | 0.4 |
| Aminopropyl phenyl trimethicone | 0.4 |
| Guar hydroxypropyltrimonium chloride | 0.1 |
| PEG-90M | 0.1 |
| Hydrolyzed elastin | 0.8 |
| Panthenol | 0.5 |
| BHT | 0.05 |
| Perfume | 0.5 |

EXAMPLE 4—STRAIGHTENING TEST 4.1—Straightening Process

The kit described in the previous Example 3 is used for straightening a frizzy, recalcitrant and indomitable hair of the Afro type, when it comes into contact with moisture.

Figure 5:
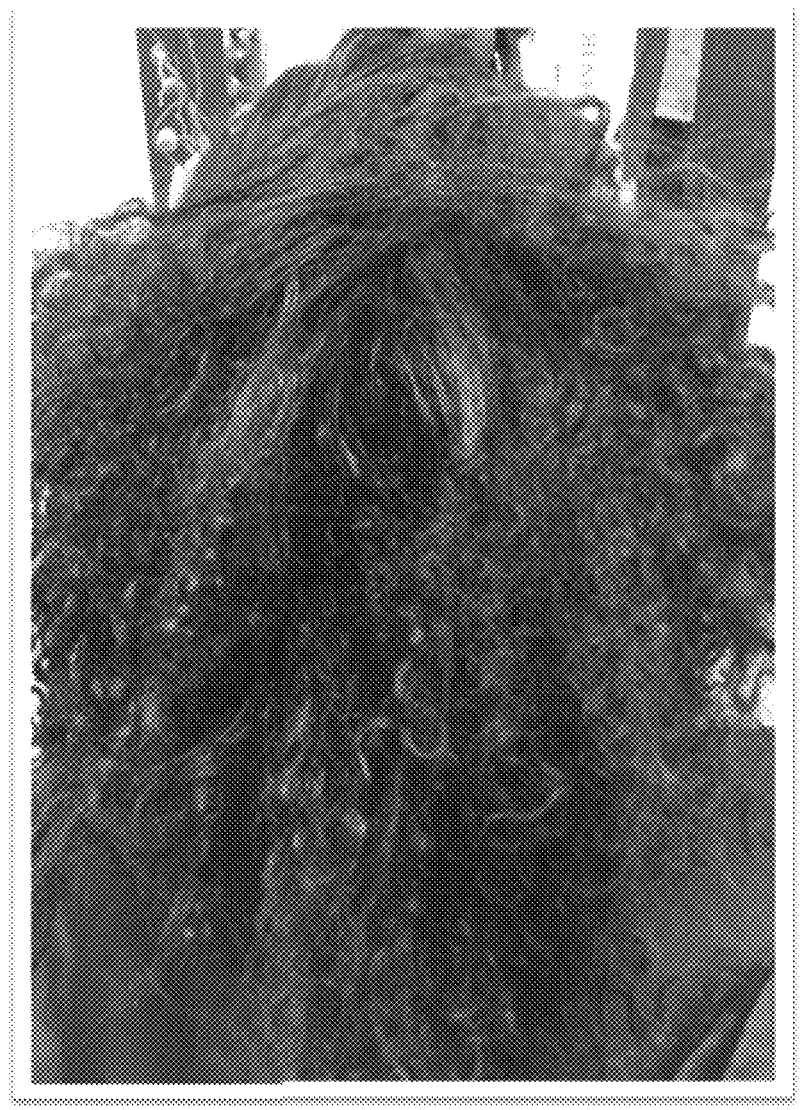
FIG. 5 shows hair before treatment with the composition according to the invention.

A photo taken before treatment shows the hair in its natural state (FIG. 5).

The application of the composition according to the invention is performed according to the following protocol.

Step 1: Application of the Straightening Cream Directly on Dry Hair

The composition according to the invention is applied strands by strands from the root to the tip. Each strand is kneaded and combed in order to properly distribute the product.

Afterwards, the hair is covered with a cellophane and the composition is left to act for 30 minutes.

Step 2: Drying

Afterwards, the hair is heated in hot air with a hair dryer, by directing the blow of air from the root to the tip to lower the cuticle. 3 cm-wide strands are selected and maintained perpendicular to the scalp in order to be heated over their entire length.

Step 3: Rinsing

The entire hair is rinsed and a classic shampoo without Sodium Laureth Sulfate (SLS) is applied.

The shampoo is rinsed off and the «top coat» mask composition is applied, then left to stand for 5 minutes and rinsed.

Step 4: Straightening

Afterwards, the hair is hand-styled with a hair dryer.

4.2—Obtained Results

It is observed that during straightening, the hair is straightened and put in place without the need to use a hair straightener.

Figure 6:
FIG. 6 shows the hair after treatment with the composition according to the invention.

A straightened hair is thus obtained simply in contact with the heat of the hair dryer, without having to resort to the effect of tension or intense heat of the hair straightener (FIG. 6).

Figure 7:
FIG. 7 shows the hair after treatment with the composition according to the invention and after steam treatment.

The fiber is mastered, including after having been subjected for a period of 15 minutes to a steam treatment with a moisture content of 91% (FIG. 7).

Furthermore, the observed effects are long lasting (about three months).

EXAMPLE 5—COMPARATIVE TEST

A kit containing:
a straightening composition in the form of a straightening cream comprising only but an amino acid and an alcohol (that is to say without protein and without vegetable oil);
and a «top coat» mask comprising a protein;
whose compositions are reported respectively in the following Tables 5 and 6 is prepared.

TABLE 5

Straightening composition

| Ingredients | Quantity (% w/w) |
|---|---|
| Water | 51.9 |
| Glycerin | 2 |
| Arginine | 1 |
| Cysteine | 1.8 |
| Glutamic acid | 0.4 |
| Alcohol | 5 |
| Caprylic capric triglyceride | 5 |
| Tocopherol | 0.5 |
| Aloe vera juice | 20 |
| Glyceryl stearate citrate | 2 |
| Hydroxypropyl starch phosphate | 3 |
| Cetearyl alcohol | 2 |
| Sodium stearoyl lactylate | 1 |
| Ceteareth-20 | 3 |
| Phenoxyethanol | 0.5 |
| Dehydroacetic acid, benzyl alcohol | 0.4 |
| Perfume | 0.5 |

TABLE 6

«top coat» mask

| Ingredients | Quantity (% w/w) |
|---|---|
| Water | 80.6 |
| Cetearyl alcohol | 3.5 |
| Cetrimonium chloride | 6.6 |
| Glycerin | 0.5 |
| Behentrimonium methosulfate, cetearyl alcohol | 2 |
| Polyquaternium-7 | 0.5 |
| Shea Butter | 2 |

TABLE 6-continued

«top coat» mask

| Ingredients | Quantity (% w/w) |
|---|---|
| Cetrimonium chloride, amodimethicone, trideceth-12 | 1 |
| Lactic acid | 0.05 |
| Phenoxyethanol | 0.4 |
| Hydrolyzed collagen | 0.4 |
| Aminopropyl phenyl trimethicone | 0.4 |
| Guar hydroxypropyltrimonium chloride | 0.1 |
| PEG-90M | 0.1 |
| Hydrolyzed elastin | 0.8 |
| Panthenol | 0.5 |
| BHT | 0.05 |
| Perfume | 0.5 |

A straightening test was subsequently performed with this composition according to a protocol identical to that described in Example 4.

Figure 8:
FIG. 8 shows the hair before straightening treatment with a straightening composition containing only an amino acid and an alcohol.

A photo taken before treatment shows the hair in its natural state (FIG. 8).

Figure 9:
FIG. 9 shows the hair after treatment with the composition containing only an amino acid and an alcohol.

After treatment, dull and dehydrated hair is observed. Furthermore, on contact with the heat of the hair dryer, the hair does not straighten but swells and takes on a very frothy appearance. Despite an attempt to recover by brushing, the result is very insufficient (FIG. 9).

The invention claimed is:

1. A kit useful for straightening hair comprising:
50 to 70 percent by weight of a first composition containing
0.1 to 20 percent by weight of an amino acid selected from the group consisting of aspartic acid, glutamic acid, asparagine, carnitine, cysteine, glutamine, histidine, leucine, isoleucine, methionine, N-phenylalanine, proline, hydroxyproline, threonine, tryptophan, tyrosine, valine, glycine, alanine, serine, beta alanine, taurine, lysine, arginine, and one of their acid or base, organic or mineral salts, and
0.1 to 20 percent by weight of a protein selected from the group consisting of creatine, hydrolyzed creatine, keratin, hydrolyzed keratin, wheat protein, hydrolyzed wheat protein, silk protein, hydrolyzed silk protein, soy protein, hydrolyzed soy protein, collagen, hydrolyzed collagen, elastin, hydrolyzed elastin, pea protein, hydrolyzed pea protein, rice protein, hydrolyzed rice protein, conchiolin protein, hydrolyzed conchiolin protein, whey protein, and hydrolyzed whey protein; and
30 to 50 percent by weight of a second composition containing
1 to 50 percent by weight of an alcohol selected from the group consisting of butanol, isopropanol, and ethanol, and
50 to 95 percent by weight of a vegetable oil selected from the group consisting of sweet almond oil, olive oil, argan oil, Haarlem oil, Babassu oil, broccoli seed oil, avocado oil, linseed oil, apricot oil, cucumber oil, nigella oil, brazil nut oil, grape seed oil, shea olein sesame oil and tomato oil.

2. The kit according to claim 1, wherein the composition containing the amino acid and the protein is in the form of a cream, gel, oil-in-water or water-in-oil emulsion, hair lotion or shampoo.

3. The kit according to claim 1, wherein the composition containing the alcohol and the vegetable oil is in the form of a cream, gel, oil-in-water or water-in-oil emulsion, hi-phasic lotion or shampoo.

* * * * *